United States Patent
Ates et al.

(10) Patent No.: US 7,563,912 B2
(45) Date of Patent: Jul. 21, 2009

(54) OXOPYRROLIDINE COMPOUNDS, PREPARATION OF SAID COMPOUNDS AND THEIR USE IN THE MANUFACTURING OF LEVETIRACETAM AND ANALOGUES

(75) Inventors: Celal Ates, Louvain-la-Neuve (BE); John Surtees, Jezus-Eik (BE); Anne-Catherine Burteau, Grand-Leez (BE); Violeta Marmon, Abingdon-Oxon (GB); Emile Cavoy, Ham-sur-Heure (BE)

(73) Assignee: UCB Pharma, S.A., Brussels (BE)

( * ) Notice: Subject to any disclaimer, the term of this patent is extended or adjusted under 35 U.S.C. 154(b) by 0 days.

(21) Appl. No.: 11/488,073

(22) Filed: Jul. 18, 2006

(65) Prior Publication Data

US 2006/0258734 A1    Nov. 16, 2006

Related U.S. Application Data

(62) Division of application No. 10/486,342, filed as application No. PCT/EP02/08717 on Aug. 5, 2002, now Pat. No. 7,122,682.

(30) Foreign Application Priority Data

Aug. 10, 2001  (EP)  ................. 01119396

(51) Int. Cl.
  *C07D 207/12*  (2006.01)
  *C07D 207/24*  (2006.01)
  *C07D 207/36*  (2006.01)
(52) U.S. Cl. .......... 548/543; 548/550; 548/551
(58) Field of Classification Search ........... 548/543, 548/550, 551
See application file for complete search history.

(56) References Cited

U.S. PATENT DOCUMENTS

| | | |
|---|---|---|
| 4,696,942 A | 9/1987 | Gobert et al. |
| 4,696,943 A | 9/1987 | Gobert et al. |
| 6,686,477 B2 | 2/2004 | Boaz et al. |
| 6,713,635 B2 | 3/2004 | Surtees et al. |
| 6,858,740 B2 | 2/2005 | Surtees et al. |

FOREIGN PATENT DOCUMENTS

| | | | |
|---|---|---|---|
| DE | 2106418 | * | 8/1971 |
| EP | 0 162 036 | | 11/1985 |
| EP | 0 165 919 | | 12/1985 |
| GB | 1 309 692 | | 3/1973 |
| WO | 01 64637 | | 9/2001 |

* cited by examiner

*Primary Examiner*—Golam M. M. Shameem
*Assistant Examiner*—Susannah Chung
(74) *Attorney, Agent, or Firm*—Wenderoth, Lind & Ponack, L.L.P.

(57) ABSTRACT

The present invention relates to an improved process for the preparation of (S)-(−)-α-ethyl-2-oxo-1-pyrrolidine acetamide and analogues thereof. The invention also relates to compounds of the general formula (6) wherein $R_1$ is methyl or ethyl; and $R_2$ is $C_2$-$C_4$ alkyl, $C_2$-$C_4$ alkenyl or $C_2$-$C_4$ alkynyl, optionally substituted by one or more halogen, and their preparation processes.

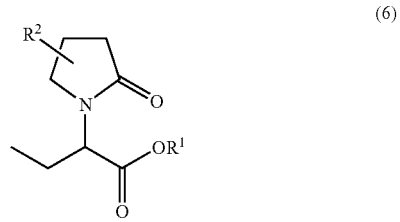

(6)

7 Claims, No Drawings

OXOPYRROLIDINE COMPOUNDS, PREPARATION OF SAID COMPOUNDS AND THEIR USE IN THE MANUFACTURING OF LEVETIRACETAM AND ANALOGUES

This is a divisional of Ser. No. 10/486,342, filed Feb. 10, 2004, now U.S. Pat. No. 7,122,682 which is a U.S. national stage of International Application No. PCT/EP02/08717 filed Aug. 5, 2002.

This invention concerns a new and improved process for the preparation of (S)-(−)-α-ethyl-2-oxo-1-pyrrolidine acetamide and analogues thereof, which is referred to under the International Non-proprietary Name of Levetiracetam. Levetiracetam is known as a useful therapeutic agent for the treatment or prevention of epilepsy and other neurological disorders. This invention also discloses novel intermediates and their use in manufacturing processes of Levetiracetam and analogues thereof.

Levetiracetam or (S)-(−)-α-ethyl-2-oxo-1-pyrrolidine acetamide, a laevorotatory compound is disclosed as a protective agent for the treatment and the prevention of hypoxic and ischemic type aggressions of the central nervous system in the European patent No. EP 0 162 036 B and has the following formula.

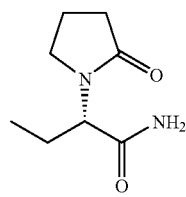

This compound is also effective in the treatment of epilepsy, a therapeutic indication for which it has been demonstrated that its dextrorotatory enantiomer (R)-(−)-α-ethyl-2-oxo-1-pyrrolidine acetamide completely lacks activity (A. J. Gower et al., Eur. J. Pharmacol., 222, 1992, 193-203). A process for the preparation of this dextrorotatory enantiomer has been described in the European patent No. 0165 919.

Manufacturing processes for Levetiracetam have been described in both the European patent No. 0162 036 and in the British patent No. 2 225 322. In the British patent No. 2 225 322 (S)-(−)-α-ethyl-2-oxo-1-pyrrolidine acetamide is prepared by hydrogenolysis of (S)-α-[2-(methylthio)ethyl]-2-oxo-1-pyrolidineacetamide in the presence of a desulfurizing reagent such as $NaBH_4/NiCl_2.6H_2O$, Raney nickel W-2 or, preferably, Raney nickel T-1. However, this process cannot be conveniently applied on an industrial scale for safety and environmental reasons.

Another industrially applicable process was developed and disclosed In a more recent patent application PCT/EP01/01956. The process described in said patent application PCT/EP01/01956 is illustrated in Scheme 1 below. This process is based on the asymmetric hydrogenation of a compound of formula (1), resulting in Levetiracetam (compound of formula (2)). Said patent application also describes the efficient asymmetric hydrogenation of related compounds of general formula (3), providing the acid and esters of general formula (4).

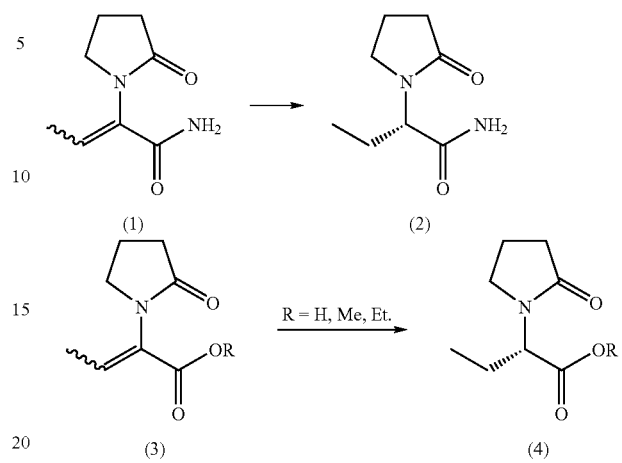

Me represents methyl, and Et represents ethyl.

However, it may be desired to convert the ester (4) directly to Levetiracetam (2) by ammonolysis. A disadvantage of performing said ammonolysis is that racemisation may occur, resulting in the formation of the compound of formula (5) as described in Scheme 2. below.

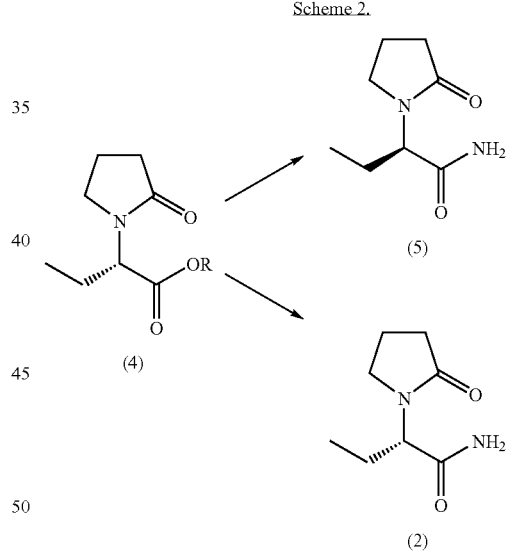

Moreover, the reaction time necessary to obtain a reasonable conversion is generally very long. The reaction time may be decreased by increasing the reaction temperature, but then the extent of racemisation increases to unacceptable levels. No compromise had until now been found between the reaction time, the temperature and extent of racemisation.

It is clear that an industrially viable process without the above-mentioned disadvantage would be extremely desirable.

The process of the present invention largely overcomes the major disadvantages such as the racemisation discussed above and excessive hydrolysis. In addition, the present invention describes novel intermediates and their use in processes for the preparation of Levetiracetam and analogues thereof. The invention also relates to new processes for preparing said intermediates.

According to a first aspect, the present invention relates to a compound of formula (6):

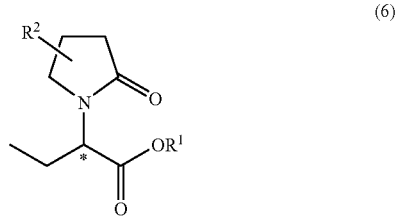

(6)

wherein $R^1$ is methyl or ethyl and $R^2$ is $C_2$-$C_4$ alkyl, $C_2$-$C_4$ alkenyl or $C_2$-$C_4$ alkynyl, optionally substituted by one or more halogen, preferably F, Cl, Br or I; as well as the stereoisomers and mixtures thereof.

This invention relates to all stereoisomeric forms such as geometrical and optical enantiomeric and diastereoisomeric forms of the compounds of formula (6) and mixtures (including racemates) thereof. The compounds of formula (6) and some of their intermediates have at least one stereogenic center in their structure, being the carbon atom attached to the nitrogen atom of the pyrrolidine heterocycle. This stereogenic center is indicated in formula (6) by an asterisk (*). This stereogenic center may be present in a R or a S configuration, said R and S notation is used in accordance with the rules described in Pure Appl. Chem., 45 (1976) 11-30. The compounds of formula (6) have at least a second stereogenic center in their structure, being the carbon atom of the pyrrolidine cycle to which the $R^2$ substituent is attached. This stereogenic center may be in a S or a R configuration. Furthermore certain compounds of formula (6) which contain alkenyl groups may exist as Z or E isomers. In each instance, the invention includes both mixtures and separate individual isomers.

The compound of the formula (6) can be in the form of a solvate, which is included within the scope of the present invention. The solvates are for example hydrates, alcoholates and the like. The compound of the formula (6) can also be in the form of a salt, especially a pharmaceutical acceptable salt, which are also included within the scope of the present invention.

According to a preferred embodiment, the present invention relates to the compound of the general formula (6), wherein the $R^2$ substituent is present at position 4 on the ring structure, as given in the following general formula (7) wherein $R^1$ and $R^2$ are as noted above.

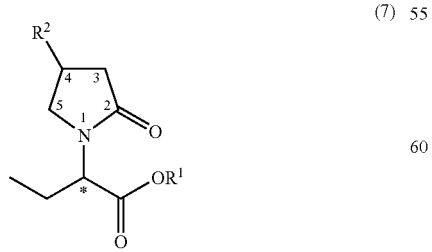

(7)

According to another preferred embodiment, the present invention relates to the compound of formula (7), wherein the $R^2$ is a C2-C4 alkyl, C2-C4 alkenyl or C2-C4 alkynyl, optionally substituted by one or more halogen.

The term alkyl as used herein includes saturated monovalent hydrocarbon radicals having straight, branched or cyclic moieties or combinations thereof.

The term alkenyl as used herein includes both branched and unbranched unsaturated hydrocarbon radicals having at least one double bond.

The term alkynyl as used herein includes both branched and unbranched hydrocarbon radicals having at least one triple bond.

According to a more preferred embodiment, the invention relates to the compound of the general formula (7), wherein $R^1$ is methyl and $R^2$ is propyl according to the following formula:

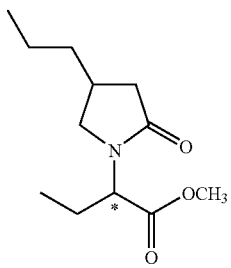

According to yet another more preferred embodiment, the invention relates to the compound of the general formula (7), wherein $R^1$ is methyl and $R^2$ is 2,2-difluorovinyl according to the following formula:

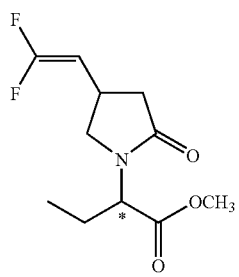

According to yet another more preferred embodiment, the invention relates to the compound of the general formula (7), wherein $R^1$ is ethyl and $R^2$ is propyl according to the following formula:

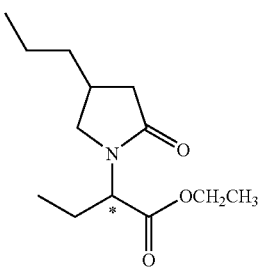

According to yet another more preferred embodiment, the invention relates to the compound of the general formula (7), wherein R¹ is ethyl and R² is 2,2-difluorovinyl according to the following formula:

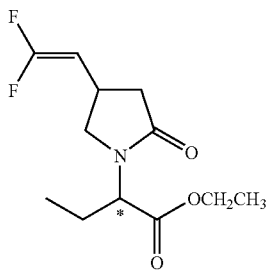

According to yet another more preferred embodiment, the invention relates to the compound of the general formula (7), wherein R¹ is methyl and R² is 2-fluoro-2-methylpropyl according to the following formula:

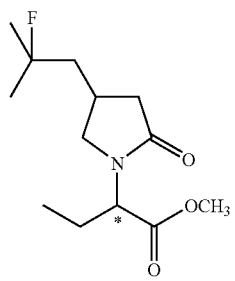

According to yet another more preferred embodiment, the invention relates to the compound of the general formula (7), wherein R¹ is ethyl and R² is 2-fluoro-2-methylpropyl according to the following formula:

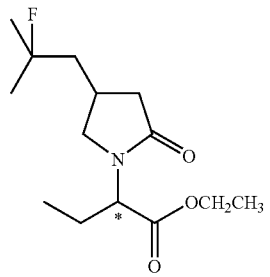

According to yet another more preferred embodiment, the invention relates to the compound of the general formula (7), wherein R¹ is methyl and R² is 2,2-difluoropropyl according to the following formula:

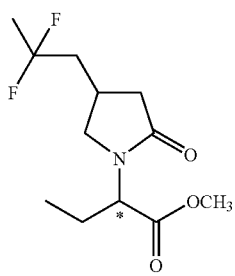

According to yet another more preferred embodiment, the invention relates to the compound of the general formula (7), wherein R¹ is ethyl and R² is 2,2-difluoropropyl according to the following formula:

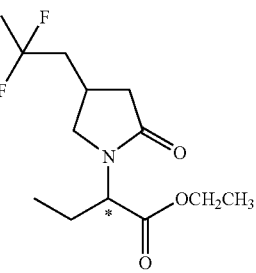

According to yet another more preferred embodiment, the invention relates to the compound of the general formula (7), wherein R¹ is methyl and R² is cyclopropylmethyl according to the following formula:

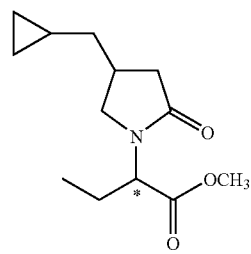

According to yet another more preferred embodiment, the invention relates to the compound of the general formula (7), wherein R¹ is ethyl and R² is cyclopropylmethyl according to the following formula:

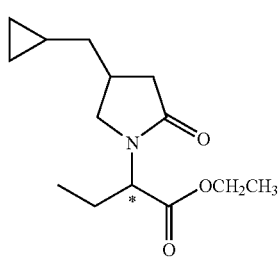

According to yet another more preferred embodiment, the invention relates to the compound of the general formula (7), wherein R¹ is methyl and R² is 2,2,2-trifluoroethyl according to the following formula:

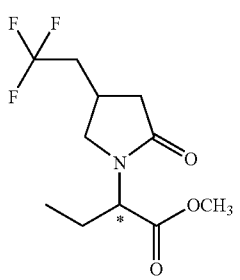

According to yet another more preferred embodiment, the invention relates to the compound of the general formula (7), wherein R¹ is ethyl and R² is 2,2,2-trifluoroethyl according to the following formula:

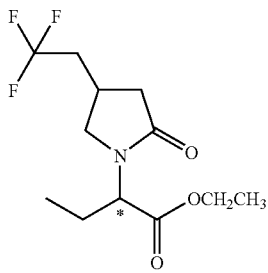

According to another preferred embodiment, the compound of general formula (6) or (7) is the S isomer as illustrated in the following formula (8) wherein R¹ and R² are as noted above.

(8)

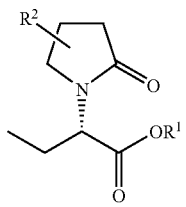

In this preferred embodiment the compounds of formula (8) include compounds wherein the second stereogenic center, that is the carbon atom of the pyrrolidine heterocycle to which the R² substituent is attached, is in a S or in a R configuration and their mixtures. Furthermore certain compounds of formula (8) which contain alkenyl groups may exist as Z or E isomers. In each instance, the invention includes both mixtures and separate individual isomers.

The invention also relates to new processes for the manufacture of said compound of the general formula (6) as defined above.

According to a first process, named the "Late Ring-Closure route or LRC route", said compound of general formula (6) of the invention as defined above may be manufactured by a process comprising following steps:

(a) reaction of a compound of formula (9)

(9)

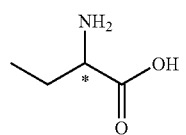

with an alcohol of formula R¹OH wherein R¹ is defied as above, (b) reaction of the corresponding compound of formula (10) thus obtained (10)

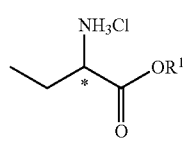

with a R²-substituted-ethyl-4-bromobutyrate wherein R² is defined as above, (c) cyclisation of the corresponding compound of formula (11) thus obtained (11)

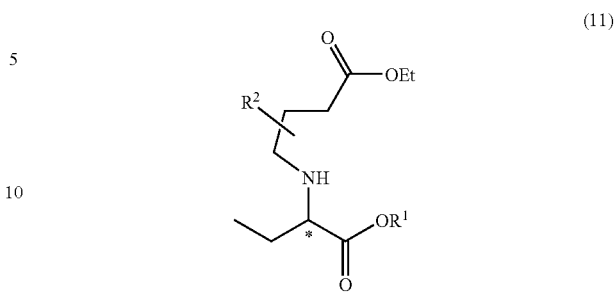

with a catalyst, and (d) isolation of the resulting compound.

In this process, the compound of formula (9) is an enantiomerically pure or an enantiomerically enriched compound, the chiral centre (either configuration) being denoted by an asterisk (*). By enantiomerically enriched compound is meant a compound containing more than 50%, preferably more than 55%, most preferably more than 60%, of one of the enantiomers. By enantiomerically pure compound is meant a compound containing at least 90%, preferably at least 95%, most preferably at least 98%, of one of the enantiomers.

The first step (step a) of this first process is preferably effectuated in the presence of an alcohol (for instance methanol or ethanol) and thionyl chloride. The second step (step b) is the mono-N-alkylation of the amino-ester of formula (10) with a R²-substituted ethyl 4-bromobutyrate (4-EBB) and is preferably effectuated in the presence of an alcohol (for instance methanol, ethanol or isopropanol). The alcohol is preferably isopropanol. The use of isopropanol resulted in a major amount of the monoalkylated ester (11) and a small amount of a dialkylated product which may be separated by column chromatography. Alternatively, the monoalkylated product may be precipitated as its hydrochloride salt by means of gaseous HCl. The hydrochloride of the mono-alkylated product (solid) is next neutralised with aqueous sodium carbonate and extracted with an organic solvent. The second step is preferably performed in the presence of base, most preferably sodium carbonate. The catalyst used in the third step (step c) in the first process is preferably 2-pyridinol. This reaction is non-racemising and provides enantiomerically enriched or pure (S)-isomers of compounds of formula (8) in the case where the (S) enantiomer of compound (9) is used as starting material.

According to an alternative process, said compound of general formula (6) of the invention as defined above may be manufactured by a process comprising the step of cyclisation of the compound of formula (11), wherein R¹ and R² are as defined above. This process is carried out according to Scheme 4. below:

Scheme 4.

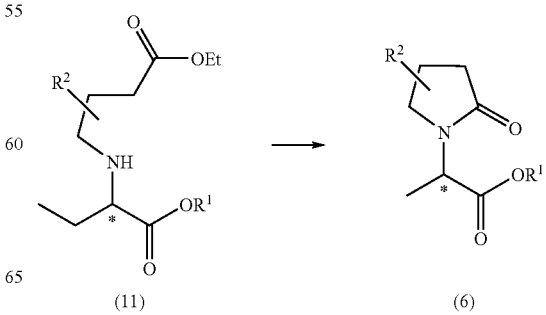

(11)                (6)

According to a second process, said compounds of formula (6) of the invention as defined above may also be manufactured by a process comprising following steps:

(a) reaction of an α-ketocarboxylic acid derivative of formula (12)

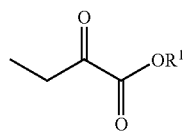

wherein $R^1$ is as defined above, with a pyrrolidinone of formula (13)

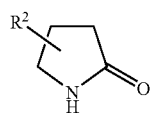

wherein $R^2$ is as defined above, (b) reaction of the corresponding compound of formula (14) thus obtained

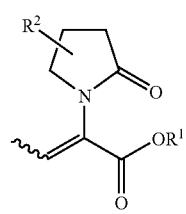

with hydrogen in the presence of an asymmetric hydrogenation catalyst, and (c) isolation the resulting compound.

This process has as a major advantage that it is much more rapid, simpler, and comprising fewer steps than the first 'LRC' route as discussed above. All details of this process are disclosed in the application PCT/EP01/01956 where it is described for compounds of a more general formula. Said application is hereby further incorporated by reference.

According to a third process, said compounds of the general formula (6) of the invention as defined above may also be manufactured by a process comprising following steps:

(a) reaction of a compound of formula (15)

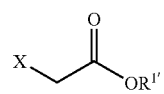

wherein $R^{1'}$ is $C_1$-$C_6$ alkyl and X is Cl, Br, I, alkylsulphonate or sulfate; with a pyrrolidone of general formula (13).

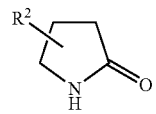

wherein $R^2$ is as noted as above;

(b) reaction of the corresponding compound of formula (16) thus obtained

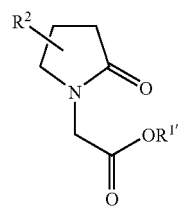

with ethyl-X, wherein X is Cl, Br, I, alkylsulphonate or sulfate and an asymmetric alkylation catalyst or additive;

(c) optionally, when $R^{1'}$ is different from $R^1$, reaction of the compound obtained from step (b) with an alcohol of formula $R^1OH$, and (d) isolating the resulting compound of formula (6).

According to this third process, $R^{1'}$ is preferably C3-C4 alkyl, especially terbutyl.

According to this third process, the asymmetric alkylation catalyst or additive is preferably a chiral amine, most preferably selected from (S)-1-(2-pyrrolidinylmethyl)-pyrrolidine (17), (R)-2-methoxyethoxyethyl-1-phenyl-2-piperidinoethylamine (18) and (S)-1-methyl-2-anilinomethyl pyrrolidine (19).

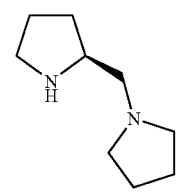

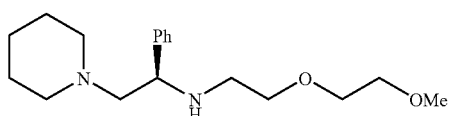

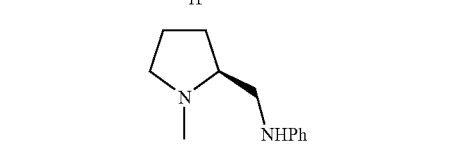

Step (b) of this third process is preferably performed in the presence of a base (such as mineral, organic or organometallic bases). The base is preferably butyllithium.

Step (c) of this process is preferably acid or base catalysed.

This process has the advantage that it comprises only few reaction steps. Another advantage is that it may be performed using inexpensive and readily available raw materials.

According to a fourth process, the compound of the general formula (6) as defined above may also be prepared by a process comprising following steps:

(a) reaction of a compound of general formula (20)

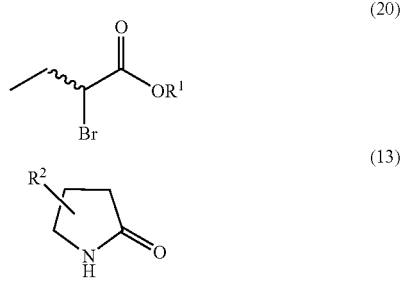

wherein R$^1$ is as defined above, with a pyrrolidone of general formula (13) wherein R$^2$ is defined as above;

(b) separation of the corresponding compound of general formula (21) thus obtained

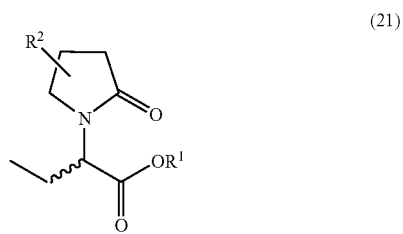

wherein R$^1$ and R$^2$ are defined as above;

(c) isolation of the resulting compound of general formula (6).

According to this fourth process, the compound of the general formula (6) as defined above may be isolated by industrial chiral chromatographic separation (batch, MCC (Multi Column Chromatography) or SMB (simulated moving bed)) of a compound of general formula (21) according to Scheme 7. below.

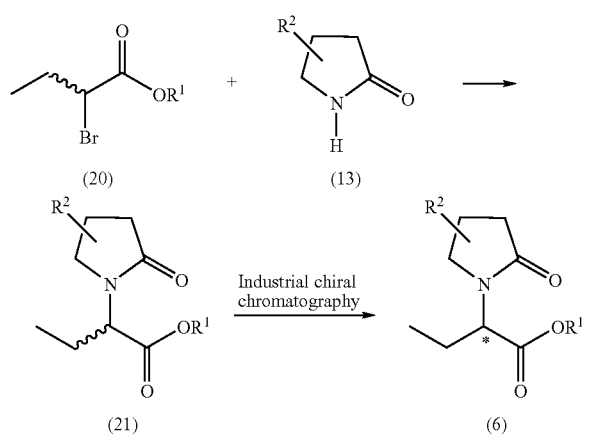

The chromatographic process can be carried out using either the batch or MCC process. Each enantiomer can be separated using a chiral stationary phase to yield enantiomerically pure products.

Commercially available chromatographic columns are for example sold by DAICEL Company or SHISEIDO Company. The preferred DAICEL columns such as the columns sold under the trademark CHIRALPAK AD, CHIRALPAK AS and CHIRALPAK OD were found to be efficient to this end when mobile phases such as mixtures of alkanes with alcohols were used or even a pure alcohol or mixtures of alcohols. The alkane or mixtures of alkanes particularly referred to are: hexane, isohexane or heptane. The alcohol or mixtures of alcohols particularly referred to are: propanol, isopropanol, ethanol or methanol. There is a preference for the use of heptane among the alkanes and there is a preference for the use of ethanol and methanol among the alcohols. There is a preference for the following mixtures: 50% to 95% for the alkane and 50% to 5% for alcohol(s), or 100% of alcohol.

The preferred SHISEIDO columns such as the columns sold under the trademark CERAMOSPHER CHIRAL RU-2 or CERAMOSPHER CHIRAL RU-1 were found to be efficient for the separation when alcohols were used as mobile phase. The alcohols referred to are: propanol, isopropanol, ethanol or methanol. There is a preference for the use of ethanol and methanol among the alcohols.

The extrapolation of small-scale batch separations of this type to an industrial scale proceeds without difficulty in either batch or continuous mode.

According to a second aspect, the present invention also relates to a process for the manufacture of a compound of the general formula (22') wherein R$^{2'}$ is hydrogen, $C_1$-$C_4$ alkyl, $C_2$-$C_4$ alkenyl or $C_2$-$C_4$ alkynyl, optionally substituted by one or more halogen, said process comprising the ammonolysis of the corresponding compound of formula (6')

Scheme 8.

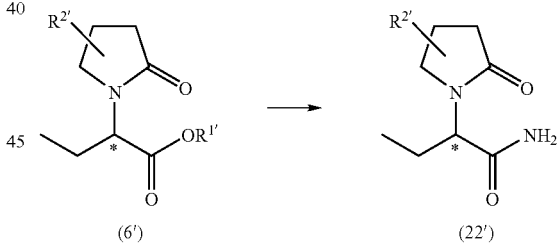

wherein R$^{1'}$ is $C_1$-$C_6$ alkyl and R$^{2'}$ is hydrogen, $C_1$-$C_4$ alkyl, $C_2$-$C_4$ alkenyl or $C_2$-$C_4$ alkynyl, optionally substituted by one or more halogen, in the presence of water.

Surprisingly, it has been found that performing said ammonolysis in the presence of water greatly overcomes the disadvantages such as racemisation as described in the background art, and encountered when using an organic solvent (e.g. methanol). Other advantage of this invention is minimisation of potential hydrolytic side-reaction.

According to a preferred embodiment, said ammonolysis as described above is performed in a mixture of water and an alcohol. Preferred alcohols are methanol, ethanol, isopropanol and butanol. Most preferably a mixture of water and methanol is used. Using a mixture of water and an alcohol, especially methanol, offers the additional advantage that the level of hydrolysis is even more decreased.

According to a preferred embodiment, said ammonolysis of the invention as described above is performed with NH$_3$. Preferably, a 10-95% (w/w) NH$_3$ solution in water is used. Most preferably, a 30-80% (w/w) NH$_3$ solution in water, especially a 50% NH$_3$ solution in water, is used.

According to yet another preferred embodiment, said ammonolysis of the invention as described above is performed at 0 to 40° C. most preferably at a temperature of 0 to 25° C., especially at a temperature of about 3 to 10° C.

In the process according to the invention, the molar ratio of NH$_3$ to the compound of formula (6') is generally at least 1, preferably at least 4, most preferably at least 6. The molar ratio does preferably not exceed 100.

According to a preferred embodiment of the process for the manufacture of the compound of formula (22'), a compound of the general formula (6') is used wherein R$^{1'}$ is methyl, ethyl or a C$_3$-C$_4$ alkyl. Especially preferred are compounds of general formula (6') wherein R$^{1'}$ is methyl or ethyl and most preferably wherein R$^{1'}$ is methyl.

According to another preferred embodiment of the process for the manufacture of the compound of formula (22'), a compound of the general formula (6') is used wherein R$^{2'}$ is hydrogen.

According to a more preferred embodiment of the process for the manufacture of the compound of formula (22') a compound of the general formula (6') is used wherein R$^{1'}$ is methyl and R$^{2'}$ is hydrogen according to the following formula:

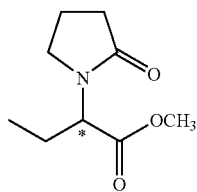

The above compound is referred to as PBM (methyl 2-(2-oxo-pyrrolidin-1-yl) butyrate).

According to yet another embodiment of the process for the manufacture of the compound of formula (22'), a compound of the general formula (6') is used wherein R$^{1'}$ is ethyl and R$^{2'}$ is hydrogen according to the following formula:

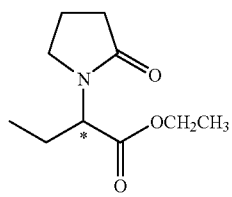

The above compound is referred to as PBE (ethyl 2-(2-oxo-pyrrolidin-1-yl) butyrate).

According to yet another embodiment of the process for the manufacture of the compound of formula (22'), a compound of the general formula (6') is used wherein the R$^{2'}$ substituent is present at position 4 on the ring structure, as given in the following general formula (7') wherein R$^{1'}$ and R$^{2'}$ are as noted above.

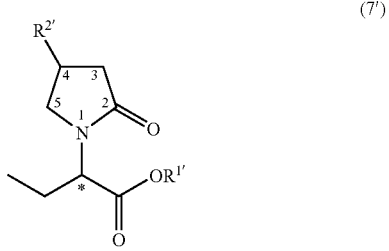

According to another preferred embodiment of the process according to the invention, the compound of formula (6') is the S isomer as illustrated in the following formula (8') wherein R$^{1'}$ and R$^{2'}$ are as noted above.

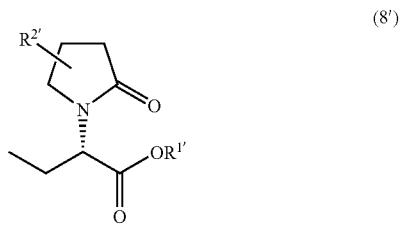

The use of an S isomer of formula (8') in the process according to the invention permits to obtain compounds of formula (22') being S isomers. Compounds of formula (6') wherein R$^{2'}$ is different from hydrogen possess a second stereogenic center, being the carbon atom of the pyrrolidine ring to which the R$^{2'}$ substituent is attached. In this case, this stereogenic center may be in an S- or R-form or mixtures of both forms may be used.

According to a more preferred embodiment of the process for the manufacture of the compound of formula (22'), a compound of the general formula (6'), (7') or (8') is used, wherein R$^{2'}$ is selected from the group of hydrogen, propyl, 2,2-difluorvinyl, 2-fluoro-2-methylpropyl, 2,2-difluoropropyl, cyclopropylmethyl and 2,2,2-trifluoroethyl.

The ammonolysis process according to the invention permits high conversion rates. The ammonolysis process according to the invention offers also the advantage that the amount of racemisation and hydrolysis is very low, even negligible. A simple crystallisation of the crude products from this ammonolysis in an organic solvent may give pure compounds, such as pure Levetiracetam.

The compound of formula (6') used as starting material in the process for the manufacture of a compound of formula (22'), can be manufactured by any process suitable therefore.

According to a first variant, the compound of formula (6') is manufactured by a first new process comprising following steps:

(a) reaction of a compound of formula (9)

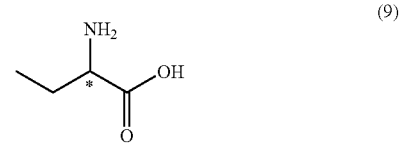

with an alcohol of formula R$^{1'}$OH wherein R$^{1'}$ is defined as above, (b) reaction of the corresponding compound of formula (10')
thus obtained

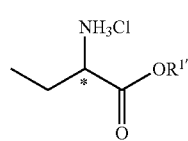

with a $R^{2'}$-substituted-ethyl-4-bromobutyrate wherein $R^{2'}$ is defined as above, (c) cyclisation of the corresponding compound of formula (11') thus obtained

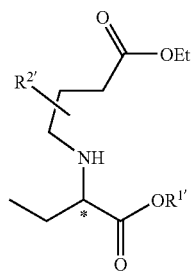

in the presence of a catalyst, and (d) isolation of the resulting compound.

In this process, the compound of formula (9) is an enantiomerically enriched or an enantiomerically pure compound, the chiral centre (either configuration) being denoted by an asterisk (*).

This first new process as such for the manufacture of a compound of formula (6') is another aspect of the present invention.

The first step (step a) of this process is preferably performed in the presence of an alcohol (for instance methanol or ethanol) and thionyl chloride. The second step (step b) of this process is the mono-N-alkylation of the amino-ester of formula (10') with a $R^{2'}$-substituted ethyl 4-bromobutyrate (4-EBB) and is preferably performed in the presence of an alcohol (for instance methanol, ethanol or isopropanol). The alcohol is preferably isopropanol. The use of isopropanol presents the further advantage that transesterification did not occur. Moreover, the use of isopropanol resulted in a major amount of the monoalkylated ester (11') and only a small amount of a dialkylated product which may be separated by column chromatography. Alternatively, the monoalkylated product may be precipitated as its hydrochloride salt by means of gaseous HCl. The hydrochloride of the mono-alkylated product (solid) is next neutralised with aqueous sodium carbonate and extracted with an organic solvent. The second step is preferably performed in the presence of base, preferably sodium carbonate. The catalyst used in the third step (step c) in the process is preferably 2-pyridinol. This reaction is non-racemising and provides enantiomerically pure (S)-compounds of formula (8') in the case where the (S) enantiomer of compound (9) is used as starting material.

According to an alternative process, said compound of general formula (6') of the invention as defined above may be manufactured by a process comprising the step of cyclisation of the compound of formula (11'), wherein $R^{1'}$ and $R^{2'}$ are as defined above. This process is carried out according to Scheme 4'. below:

Scheme 4'.

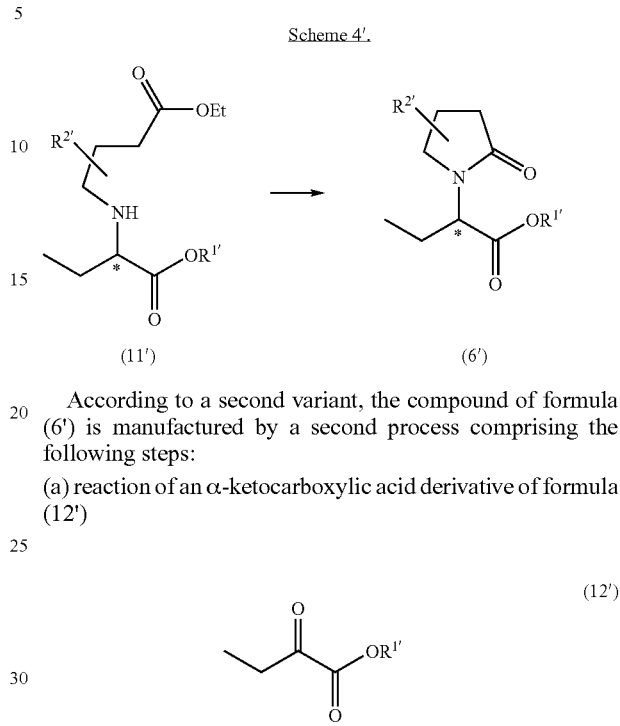

According to a second variant, the compound of formula (6') is manufactured by a second process comprising the following steps:

(a) reaction of an α-ketocarboxylic acid derivative of formula (12')

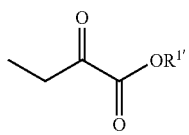

wherein $R^{1'}$ is as defined above with a pyrrolidinone of formula (13')

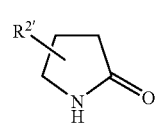

wherein $R^{2'}$ is as defined above, (b) reaction of the corresponding compound of formula (14') thus obtained

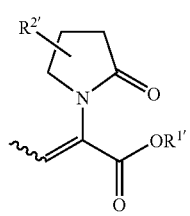

wherein $R^{1'}$ and $R^{2'}$ are defined as above, with hydrogen in the presence of an asymmetric hydrogenation catalyst;

(c) isolation of the resulting compound.

This second process has as a major advantage that it is much more rapid and simpler, comprising fewer steps than the first 'LRC' route as discussed above. All details of this process are disclosed in the application PCT/EP01/01956 where it is described for compounds of a more general formula. Said application is hereby further incorporated by reference.

According to a third variant, compounds of the general formula (6') as defined above are manufactured by a third new process comprising following steps:

(a) reaction of a compound of formula (15')

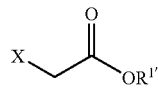
(15')

wherein $R^{1'}$ is as noted above and X is Cl, Br, I, alkylsulphonate or sulfate; with a pyrrolidone of general formula (13')

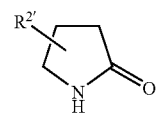
(13')

wherein $R^{2'}$ is as noted as above;

(b) reaction of the corresponding compound of formula (16') thus obtained

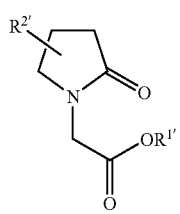
(16')

with ethyl-X, wherein X is Cl, Br, I, alkylsulphonate or sulfate in the presence of an asymmetric alkylation catalyst or additive;

(c) isolation of the resulting compound of formula (6').

According to this third variant, $R^{1'}$ is preferably $C_3$-$C_4$ alkyl, especially tertbutyl.

This third new process as such for the manufacture of a compound of formula (6') is another aspect of the present invention.

According to this third process, the asymmetric alkylation catalyst or additive is preferably a chiral amine, most preferably selected from (S)-1-(2-pyrrolidinylmethyl)-pyrrolidine (17), (R)-2-methoxyethoxyethyl-1-phenyl-2-piperidinoethylamine (18) and (S)-1-methyl-2-anilinomethyl pyrrolidine (19).

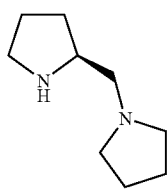
(17)

-continued

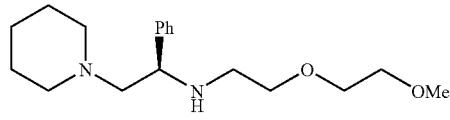
(18)

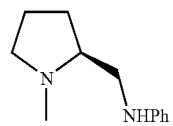
(19)

Step (b) of this process is preferably performed in the presence of a base (such as mineral, organic or organometallic bases). This base is most preferably butyllithium.

Especially when $R^{1'}$ is not methyl or ethyl, this third process may comprise an additional reaction step wherein the compound obtained from step (b) is reacted with an alcohol of formula $R^1OH$ wherein $R^1$ is methyl or ethyl, preferably in the presence of an acid, so that a compound of formula (6') is formed wherein $R^{1'}$ is methyl or ethyl.

This third process has the advantage that it comprises only few reaction steps. Another advantage is that it may be performed using inexpensive and readily available raw materials.

According to a fourth variant, the compound of the general formula (6') as defined above is prepared by a fourth new process comprising following steps:

(a) reaction of a compound of general formula (20')

(a) reaction of a compound of general formula (20')

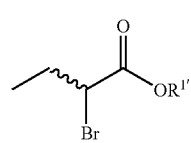
(20')

wherein $R^{1'}$ is as noted above, with a pyrrolidone of general formula (13')

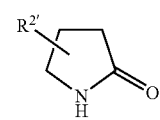
(13')

wherein $R^{2'}$ is defined as above;

(b) separation of the corresponding compound of general formula (21') thus obtained wherein $R^{1'}$ and $R^{2'}$ are defined as above; and

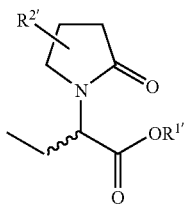

(c) isolation of the resulting compound of general formula (6').

This fourth new process as such for the manufacture of a compound of formula (6') is another aspect of the present invention.

According to this fourth process, the compound of the general formula (6') as defined above is preferably isolated by industrial chiral chromatographic separation (batch, MCC (Multi Column Chromatography) or SMB (simulated moving bed)) of a compound of general formula (21') according to Scheme 7'. below.

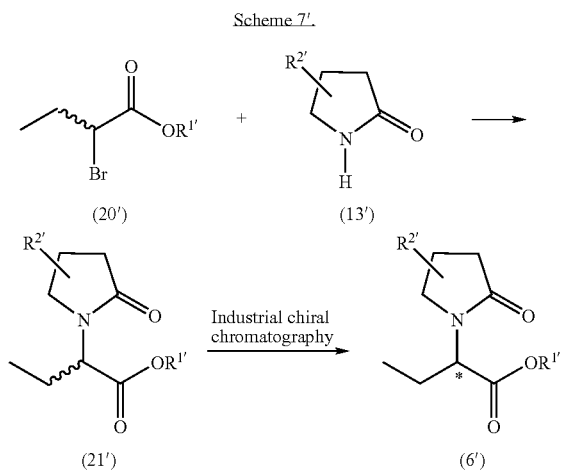

According to this fourth process, (S)-PBE and (S)-PBM can be separated using chiral HPLC by means of commercially available chiral stationary phases. These separations can more particularly be performed using chromatographic columns sold by DAICEL Company or SHISEIDO Company. The chromatographic process can be carried out using either the batch or MCC process. Each enantiomer can be separated using a chiral stationary phase to yield enantiomerically pure (S)-PBM and (S)-PBE.

The preferred DAICEL columns such as the columns sold under the trademark CHIRALPAK AD, CHIRALPAK AS and CHIRALPAK OD were found to be efficient to this end when mobile phases such as mixtures of alkanes with alcohols were used or even a pure alcohol or mixtures of alcohols. The alkane or mixtures of alkanes particularly referred to are: hexane, isohexane or heptane. The alcohol or mixtures of alcohols particularly referred to are: propanol, isopropanol, ethanol or methanol. There is a preference for the use of heptane among the alkanes and there is a preference for the use of ethanol and methanol among the alcohols. There is a preference for the following mixtures: 50% to 95% for the alkane and 50% to 5% for alcohol(s), or 100% of alcohol.

The preferred SHISEIDO columns such as the columns sold under the trademark CERAMOSPHER CHIRAL RU-2 or CERAMOSPHER CHIRAL RU-1 were found to be efficient for the separation when alcohols were used as mobile phase. The alcohols referred to are: propanol, isopropanol, ethanol or methanol. There is a preference for the use of ethanol and methanol among the alcohols.

The extrapolation of small-scale batch separations of this type to an industrial scale proceeds without difficulty in either batch or continuous mode.

The optimum conditions as determined by chiral HPLC for the separation of both PBE & PBM are presented in Tables I and III below. An estimated productivity for PBE and PBM using the MCC process is also given in Tables II and IV.

TABLE I

Examples of separation by chiral HPLC: PBM

| Phase provider | Phase | Solvents | k'1 | Alpha | Resolution |
|---|---|---|---|---|---|
| Daicel | Chiralpak ® AD | Ethanol 50%/i-Hexane 50% | 0.499 | 1.19 | 1.06 |
| Daicel | Chiralpak ® AD | Ethanol 2%/Methanol 8%/Hexane90% | 2.432 | 1.45 | 2.1 |
| Daicel | Chiralpak ® AD | Acetonitrile 100% | 0.549 | 1.3 | 0.79 |
| Daicel | Chiralpak ® AD | Ethanol 10%/Heptane 90% | 3.901 | 1.24 | 1.19 |
| Daicel | Chiralpak ® AD | Ethanol 5%/Methanol 5% Heptane 90% | 3.646 | 1.41 | 1.92 |
| Daicel | Chiralpak ® AS | i-Propanol 10%/i-Hexane 90% | 9.408 | 1.28 | 2.6 |
| Daicel | Chiralpak ® AS | Ethanol 10%/i-Hexane 90% | 3.035 | 1.17 | 1.65 |
| Daicel | Chiralpak ® AS | Propanol 10%/i-Hexane 90% | 2.987 | 1.14 | 1.34 |
| Daicel | Chiralpak ® OD-H | Ethanol 5%/i-Hexane 95% | 2.49 | 1.23 | 2.97 |
| Daicel | Chiralpak ® OD-H | Propanol 5%/i-Hexane 95% | 1.94 | 1.22 | 2.58 |
| Shiseido | Ceramospher Chiral RU-1 | Methanol 100% | 4.69 | 1.28 | 1.56 |
| Shiseido | Ceramospher Chiral RU-2 | Methanol 100% | 3.747 | 1.29 | 1.5 |
| Shiseido | Ceramospher Chiral RU-2 | Ethanol 100% | 4.853 | 1.32 | 1.19 |

TABLE II

Estimated productivity using MCC process: PBM

| Phase provider | Phase | Solvents | Productivity (kg/kg/day) |
|---|---|---|---|
| Daicel | Chiralpak ® AD | Ethanol 2%/ Methanol 8%/ i-Hexane 90% | 0.17 |

Productivity as presented in the above table is expressed as Kg of racemic PBM engaged per Kg of chiral stationary phase per day.

TABLE III

Examples of separation by chiral HPLC: PBE

| Phase provider | Phase | Solvents | k'1 | Alpha | Resolution |
|---|---|---|---|---|---|
| Daicel | Chiralpak ® AD | Ethanol 50%/i-Hexane 50% | 0.449 | 1.3 | 1.15 |
| Daicel | Chiralpak ® AD | Ethanol 2%/Methanol 8%/Hexane 90% | 1.955 | 1.9 | 3.32 |
| Daicel | Chiralpak ® AD | Acetonitrile 100% | 0.554 | 1.8 | 2.05 |
| Daicel | Chiralpak ® AD | Ethanol 10%/Heptane 90% | 3.076 | 1.5 | 4.4 |
| Daicel | Chiralpak ® AD | Ethanol 5%/Methanol 5% Heptane 90% | 2.971 | 1.7 | 2.93 |
| Daicel | Chiralpak ® AD | Methanol 5%/Benzine 95% | 3.227 | 1.7 | 2.99 |
| Daicel | Chiralpak ® AD | i-Propanal 10%/i-Hexane 90% | 5.029 | 2.16 | 7.39 |
| Daicel | Chiralpak ® AD | Ethanol 10%/i-Hexane 90% | 1.764 | 1.9 | 5.97 |
| Daicel | Chiralpak ® AD | Propanol 10%/i-Hexane 90% | 1.733 | 1.86 | 5.46 |
| Daicel | Chiralpak ® AD | Ethanol 5%/i-Hexane 95% | 1.878 | 1.13 | 1.66 |
| Daicel | Chiralpak ® AD | Propanol 5%/i-Hexane 95% | 1.44 | 1.14 | 1.56 |
| Shiseido | Ceramospher Chiral Ru-1 | Methanol 100% | 5.047 | 1.89 | 3.57 |
| Shiseido | Ceramospher Chiral Ru-2 | Methanol 100% | 3.869 | 1.84 | 3.21 |
| Shiseido | Ceramospher Chiral Ru-2 | Ethanol 100% | 3.97 | 2.01 | 1.94 |

TABLE IV

Estimated productivity using MCC process: PBE

| Phase provider | Phase | Solvents | Productivity (kg/kg/day) |
|---|---|---|---|
| Daicel | Chiralpak ® AD | Ethanol 10%/Heptane 90% | 0.84 |

Productivity as presented in the above table is expressed as Kg of racemic PBE engaged per Kg of chiral stationary phase per day.

In the implementation of the processes according to the invention, the reaction products may be isolated from the reaction medium and, if necessary, further purified according to methodologies generally known in the art such as, for example extraction, crystallisation, distillation and chromatography, or any combination of the same.

Stereoisomerically pure forms of said compounds of the invention (and said intermediates) can be obtained by the application of procedures known to a chemist skilled in the art. For example, diastereoisomers can be separated by physical methods such as selective crystallisation or chromatographic techniques, e.g. counter current distribution, liquid chromatography and related methods. Enantiomers can be obtained from racemic mixtures by first converting said racemic mixtures with suitable resolving agents such as, for example, chiral acids, to mixtures of diastereoisomeric salts or compounds; then physically separating said mixtures of diastereoisomeric salts or compounds by, for example, selective crystallisation or chromatographic techniques, e.g. liquid chromatography and related methods; and finally converting said separated diastereomeric salts or compounds into the corresponding enantiomers.

Alternatively, pure stereochemically isomeric forms may be obtained by using enantioselective reactions according to procedures known by the person skilled in the art.

Another alternative manner of separating the enantiomeric forms of the compounds of formula (6) or (6') and intermediates involves liquid chromatography, in particular liquid chromatography using a chiral stationary phase.

According to another aspect, the present invention also relates to any compounds obtained by a process of the invention as defined above. In particular, the invention comprises Levetiracetam obtained by said processes. More particularly, the present invention also relates to new compounds obtainable by the processes according to the invention such as compounds of formula (22') wherein $R^{2'}$ is 2-fluoro-2-methylpropyl or cyclopropylmethyl. More specifically the present invention also relates to the (4S) and (4R) diastereoisomers of (2S)-2-[4-(2-fluoro-2-methylpropyl)-2-oxo-1-pyrrolidinyl] butanamide and of (2S)-2-[4-cyclopropylmethyl)-2-oxo-1-pyrrolidinyl]butanamide, and pharmaceutical compositions containing such compounds and their use as pharmaceuticals.

The following examples serve to illustrate the invention and therefore should not be taken to limit the scope thereof.

EXAMPLES

Example 1

Step 1—Synthesis of methyl (S)-aminobutyrate hydrochloride

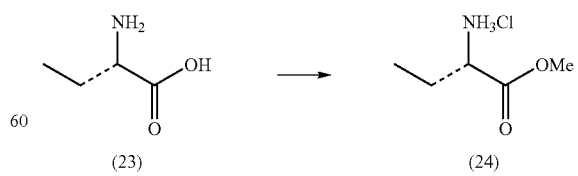

5.0 g of (S)-amino butyric acid (23) was suspended in 50 ml of methanol and stirred at 0-5° C. 6.35 g of thionyl chloride was added dropwise over 45 min to form a clear solution. After stirring for 20 hours at room temperature, the reaction was concentrated under reduced pressure to dryness and the almost colourless residue solidified to give the required product which was dried in an oven at 50° C. under vacuum (7.6 g; 102% crude yield). The same reaction was scaled-up from 200 g of the amino acid and provided 296 g (99.5% yield) of product (24).

Analysis gave the following results:
1H NMR (DMSO-$d_6$): d 0.94 (3H, t) 1.88 (2H, q) 3.75 (3H, s) 3.9 (1H, m) 8.8 (3H, m).
m.p.: 107° C.-110° C.
IR: 2876 cm$^{-1}$, 1742 cm$^{-1}$.
TLC: $SiO_2$, 20% MeOH/80% EtOAc/1% $NH_4OH$, UV & IR.
(TLC is an abbreviation for thin layer chromatography).

Step 2—Synthesis of methyl (S)-aminobutyrate-N(4-ethylbutyrate)

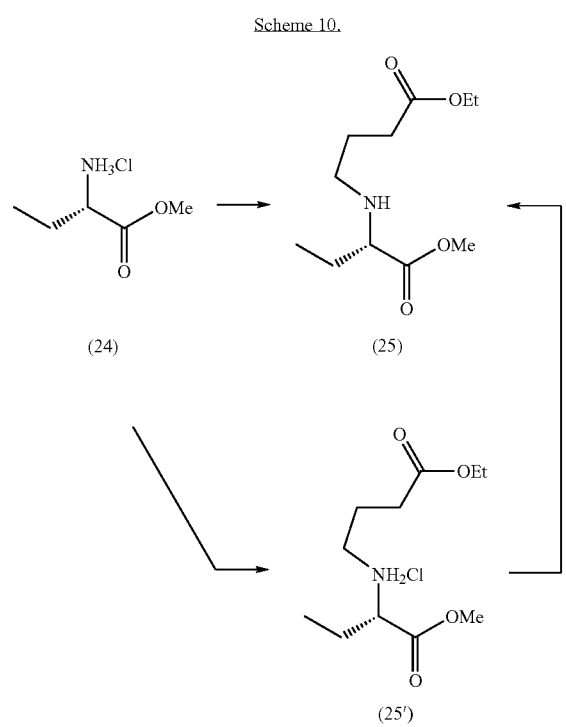

2.0 g of (S)-aminobutyrate hydrochloride salt (24) was dissolved and stirred at room temperature in 20 ml of 2-propanol, followed by addition of 2.8 g of sodium carbonate and the reaction was then heated to reflux. When reflux temperature was reached, 2.8 g of 4-BBE (ethyl-4-bromobutyrate) was added dropwise over a period of 10 min, with reflux and stirring being maintained for 24 hrs. The reaction medium was allowed to cool to room temperature, the salts were filtered and rinsed with 50 ml of 2-propanol. Following this alkylation the desired product (25) may be isolated and purified either by chromatography or via the hydrochloride salt (25') as depicted in Scheme 10. above and as described in Methods A and B below.

(Method A): The filtrate was concentrated under reduced pressure to give 3.0 g of a pale yellow liquid. This liquid was purified by chromatography through 125 g of silica and eluted with a 50/50 mixture of hexane/ethyl acetate to provide the required 2.45 g (81% yield) mono alkylated ester (25) (Method B): Chromatography can be avoided if the corresponding hydrochloride salt is generated, precipitated and filtered from a mixture of isopropanol and DIPE (di-isopropylether). Treatment of this salt (25') with sodium carbonate in water and extraction with ethyl acetate and concentration provides the pure free base (25) (the required mono alkylated ester) as a liquid.

Analysis gave the following results:
$^1$H NMR (CDCl$_3$): d 0.9 (3H, t) 1.2 (2H, t) 1.4 (1H, s) 1.5-1.7 (4H, m) 2.3-2.7 (4H, m) 3.15 (1H, t) 3.7 (3H, s) 4.1 (2H, q).

The identity of the product is confirmed by GC-MS, TLC.
IR: 2938 cm$^{-1}$, 1730 cm$^{-1}$.
TLC: $SiO_2$, 50% Hexane/50% EtOAc, UV & IR.

Step 3—Synthesis of methyl (S)-pyrrolidino-butyrate (26) [(S)-PBM)]

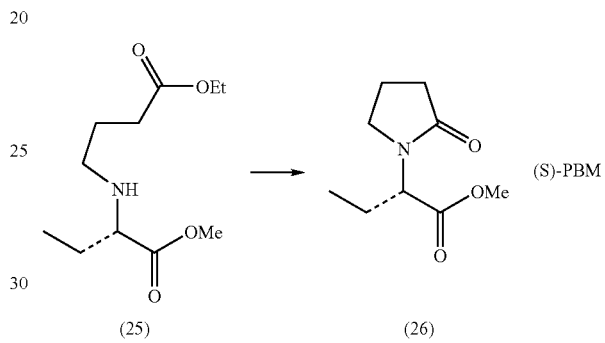

1.0 g of compound (25) and 2-pyridinol (0.02 g; 5 mol %) were magnetically stirred in 5 ml of toluene at reflux for 24 hrs. The reaction mixture was allowed to cool to room temperature and TLC analysis showed almost complete conversion. The reaction mixture was then evaporated under reduced pressure to leave crude (S)-PBM (26) as a pale brown liquid (1.0 g).

The identity of the product was confirmed by GC-MS, TLC, HPLC (Chiral and Achiral) using external references.

Step 4—Ammonolysis of (S)-PBM to give Levetiracetam

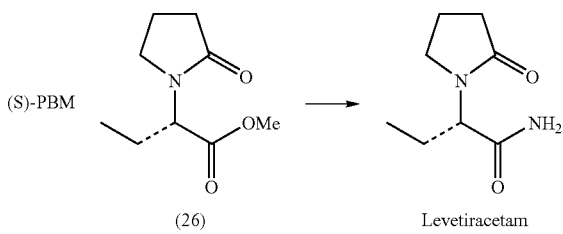

11.3 g of ammonia gas was condensed in 13.2 ml of water at approximately 0° C. and the temperature was maintained at 0-5° C. Then 20 g of (S)-PBM (26) was added dropwise over a period of 10 min and reaction mixture was maintained at 5° C. and stirred for minimum 8 hrs (reaction was complete as indicated by TLC). The reaction mixture was then evaporated to dryness under vacuum and dried by means of toluene (2×50 ml) to give minimum 17 g (92%) of crude (S)-pyrrolidinobutyramide (crude Levetiracetam) as an off-white to beige solid.

Analysis gave the following results (chiral and achiral HPLC): The extent of racemisation was 0.0%. The extent of hydrolysis was measured to 2.5%.

Example 2

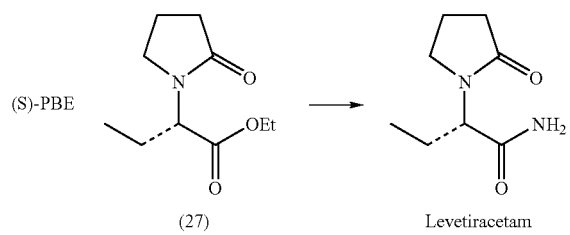

17.3 g of ammonia gas were condensed in 22 ml of water at 0° C. and temperature maintained at 0-5° C. Then 20 g of (S)-PBE obtained via SMB separation of the corresponding racemic mixture were added dropwise over a period of 2 min and the reaction mixture was maintained at 5° C. and stirred for 96 hrs (reaction was complete as Judged by TLC). The reaction mixture was then evaporated to dryness under vacuum and dried by means of toluene (2×100 ml) to give minimum 14.8 g (87%) of crude (S)-pyrrolidinobutyramide as a brown orange solid. Analysis gave the following results (chiral and achiral HPLC): The extent of racemisation was 1.6% with 6.6% hydrolysis.

Example 3

10.3 g of ammonia gas were condensed in 13.2 ml water at 0° C. and the temperature of the system was maintained at 0-5° C. 20 g of (S)-PBE obtained via asymmetric hydrogenation was then added dropwise over a period of 10 min, maintaining the reaction mixture at 5° C. The system was then stirred for 96 hrs, with TLC indicating completion of reaction. The reaction mixture was then evaporated to dryness under vacuum and dried by means of toluene (2×50 ml) to give minimum 15.7 g (92%) of crude (S)-pyrrolidinobutyramide as a brown orange solid. Analyses gave the following results (chiral and achiral HPLC): The extent of racemisation was 0.2% with 3.4% hydrolysis.

Example 4

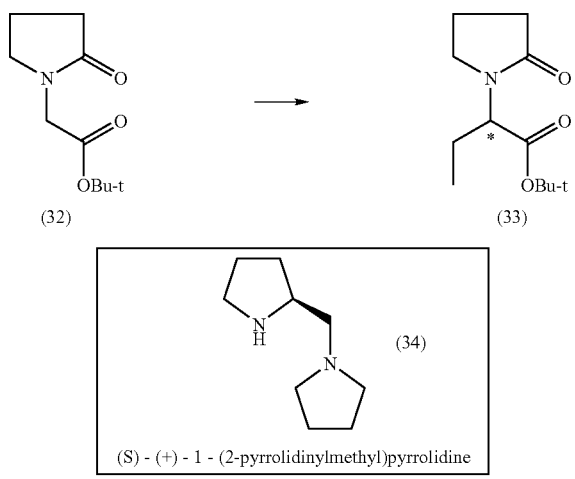

A reaction flask was charged with the chiral amine (34) (1.07 equivalent (eq.); and anhydrous toluene (15 vol) with stirring under an inert atmosphere. The solution was cooled below −70° C. and BuLi (2.5M in hexane, 1.04 eq.) was added dropwise. The reaction mixture was stirred for 30 min at this temperature, then at −10° to 0° C. for 10 min. A solution of t-butyl 2-(2-oxopyrrolidin-1-yl)-acetate (32) (600 mg, 1 eq., 1 wt) in toluene (5 vol) was added slowly, keeping the reaction temperature below −70° C. The reaction mixture was stirred at −40 to −50° C. for 30 min. Ethyl iodide 2.5 eq., 1 vol) was then added and the reaction mixture was stirred at −50 to −40° C. for 3 hrs. After being kept in the freezer at approximately −40° C. overnight, the reaction mixture was diluted with pH 7 buffer ($KH_2PO_4$/KOH. 1M, 33 vol) and dichloromethane (33 vol). The aqueous phase was extracted with dichloromethane (3×16 vol) and the combined organic extracts were then dried over $MgSO_4$ and concentrated in vacuo to give crude material. Purification of this crude product using flash chromatography ($SiO_2$, 40 wt) with hexane/EtOAc eluent gave the desired alkylated product (33) in 78% yield.

1H-NMR in $CDCl_3$: δ 0.85t(3H), 1.4s(9H), 1.5-1.7m(1H), 1.9-2.0m(3H), 2.45m(2H), 3.25m (1H), 3.5m(1H), 4.5dd (1H)

HPLC analysis: t-Butyl 2-(2-oxopyrrolidin-1-yl)-butanoate (25 mg) was accurately weighed into a 25 ml volumetric flask. Mobile phase (99:1 hexane/isopropanol, 20 ml.) was added and the sample was dissolved using ultrasonication. After cooling to ambient temperature the concentration was adjusted with mobile phase to give a working concentration of 1 mg/ml. The analysis was conducted using a column sold under the trademark CHIRACEL OD (4.6×250 mm, DAICEL), flow rate of 1 ml/min, UV detection at 250 nm and injection volume of 20 μl at ambient temperature. The relative retention times of the two enantiomers was 17.9 and 22.3 minutes TLC conditions: $SiO_2$ in EtOAc; visualisation with $KMnO_4$.

Example 5

1. Evaluation of type of solvent most suitable for ammonolysis of (S)-PBE.

The ammonolysis of (S)-PBE was investigated in the presence of water, toluene, methanol and ethyl acetate. It was shown that the ammonolysis of (S)-PBE can only be successfully realized in the presence of water. When using methanol, the reaction is very slow and when using the other solvents mentioned above the extent of reaction is minimal.

2. Evaluation of optimum reaction temperature for the ammonolysis of (S)-PBE to form Levetiracetam.

The ammonolysis of (S)-PBE was carried out either at room temperature or at 40° C. using (S)-PBE (1 equivalent) in the presence of water (6.5 volume) and various concentrations of $NH_3$ (15, 10, 7, 5, and 2 equivalents). The reactions were carried out at room temperature and 40° C., being followed by TLC for at least 24 hours. At the end of the reaction the extent of racemisation and hydrolysis was determined by HPLC.

It was shown that:

good conversion was obtained, especially when at least 4 equivalents of $NH_3$ (per eq. of (S)-PBE) were used;

the extent of racemisation did not exceed 8% at 40° C. and decreased with reaction temperature. At temperatures between 0 and 25° C. the extent of racemisation was less than 3%;

the amount of hydrolysis was low, especially at higher molar ratios of $NH_3$ to (S)-PBE.

3. Evaluation of different concentrations of $NH_3$ for ammonolysis of (S)-PBE.

Six experiments were performed in a 100 ml reactor while varying the concentration of $NH_3$ and reaction temperature.

(S)-PBE (1 equivalent) was mixed with 10 equivalents of NH$_3$ from either a commercial solution of NH$_3$ (28% w/w) or a more concentrated solution (±50% w/w). The temperatures used were either 5, 10 or 20° C. The reaction was followed by TLC until no (S)-PBE remained and the extent of hydrolysis and racemisation was determined by HPLC.

It was shown that:

a more concentrated solution of NH$_3$ did not substantially Influence the extent of racemisation.

the extent of racemisation was always less than 3% at all reaction temperatures which were tested, the extent of racemisation increases only very moderately between 5 and 20° C., the extent of hydrolysis was low, especially when using concentrated NH$_3$ solution (±50% w/w).

the extent of racemisation is always lower at lower reaction temperature.

In summary, the following conclusions can be made:

the ammonolysis can easily be performed in the presence of water (containing preferably at least 4 equivalents of NH$_3$), this reaction does not require any catalyst and may be performed in less than 24 hours, the extent of racemisation is low (less than 3% when reaction temperature is less than 20° C.), and concentration of NH$_3$ was found to have only a minor influence on the racemisation, the extent of hydrolysis can be reduced in an even more substantial way when using a more concentrated solution of NH$_3$ (±50% w/w) at low reaction temperature (reaction takes less than 48 hours).

Example 6

(S)-PBE was reacted under the conditions specified in Table VI. The results are summarised in Table VI. below.

TABLE VI

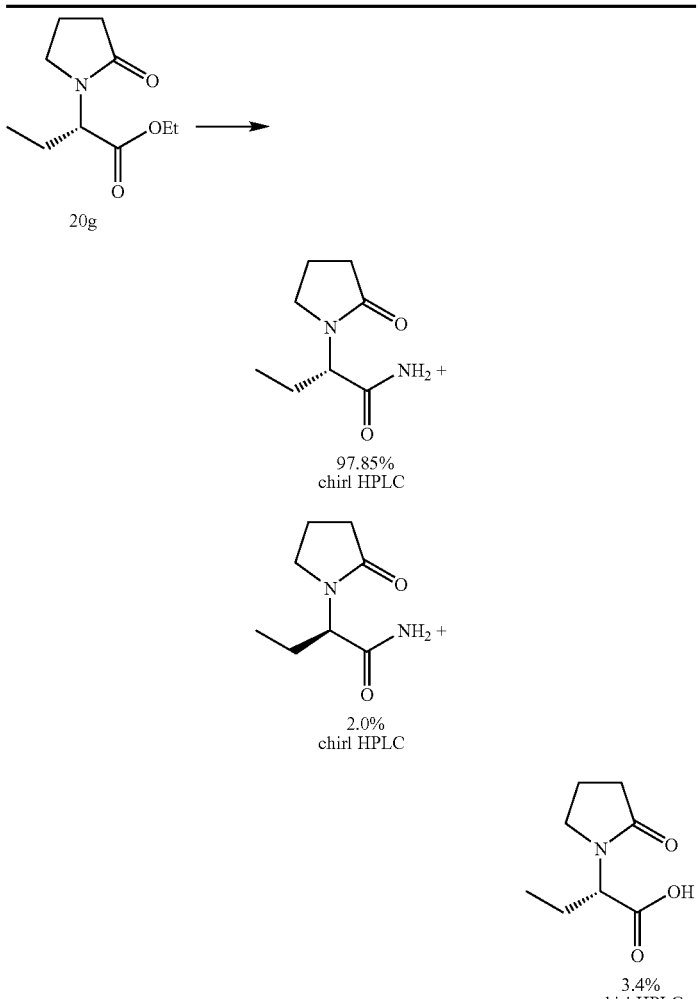

| N° Exp. | (S) PBE (g.) | NH$_3$ (eq.) | H$_2$O (Vol.) | Time (hrs) | T° (° C.) | acid (% area) | Levetiracetam or (S)-Amide (% area) | (R)-Amide (% area) |
|---|---|---|---|---|---|---|---|---|
| 6 | 20 | 6.2 | 0.66 | 96h00 | 5 | 3.44 | 97.85 | 2.00 |

The starting material contained 1.6% of the (R)-enantiomer and 98.4% of the (S)-enantiomer. The difference in enantiomeric purity between the starting material and the final amides obtained was 0.4%. This result corresponds to the degree of racemisation accompanied by said ammonolysis.

The product obtained from the experiment described above was recrystallised in eight volumes of acetone and filtered at 2° C. to give the final product, (S)-(−)-α-ethyl-2-oxo-1-pyrrolidine acetamide or Levetiracetam in 69.1% yield. The recrystallised product contained 0.11% of the (R)-amide product and 0.08% of hydrolysed product.

Example 7

(S)-PBM was reacted under the conditions specified in Table VIII. The results are summarised in Table VIII. below.

The starting material contained 96.3% of the (S)-enantiomer and 3.5% of the (R)-enantiomer. The difference in enantiomeric purity between the final product Levetiracetam and the starting material (S)-PBM was approximately 0.2%, indicating indeed that the ammonolysis is accompanied by a negligible racemisation in this case.

The final product obtained from the experiment above was recrystallized from eight volumes of acetone and filtered at 4° C. Levetiracetam is obtained in 73.3% yield. The recrystallized product contained 1.64% of the opposite enantiomeric amide and 0.03% of the hydrolysed product. Recrystallisation in the presence of acetone as described allows production of Levetiracetam of a sufficient quality for commercial purposes.

The same reaction was finally performed on an increased scale according to Scheme 18. below. Racemisation was as previously observed negligible (0.2%).

TABLE VIII

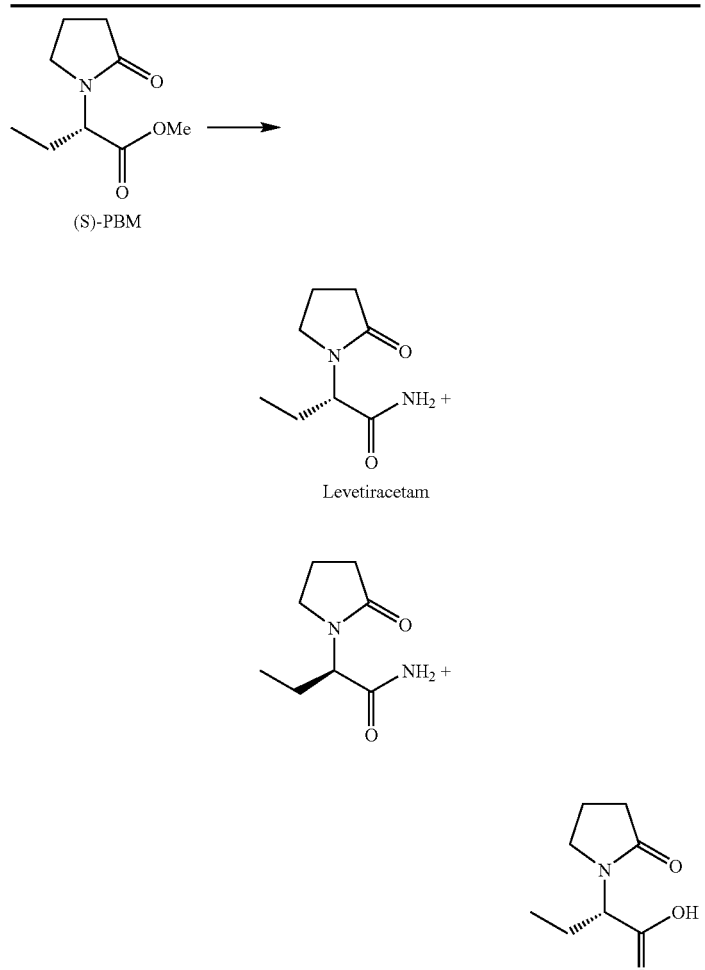

| | Reaction conditions | | | | | HPLC Analysis area % | | |
|---|---|---|---|---|---|---|---|---|
| N° Exp. | (S)-PBM (g) | NH₃ (eq.) | H₂O (Vol.) | Time (hrs) | T° (° C.) | acid (% area) | Levetiracetam (S)-amide (% area) | Opposite (R)-amide (% area) |
| 22 | 22 | 6.0 | 0.66 | 16h40 | 5 | 3.68 | 96.31 | 2.53 |

Scheme 18.

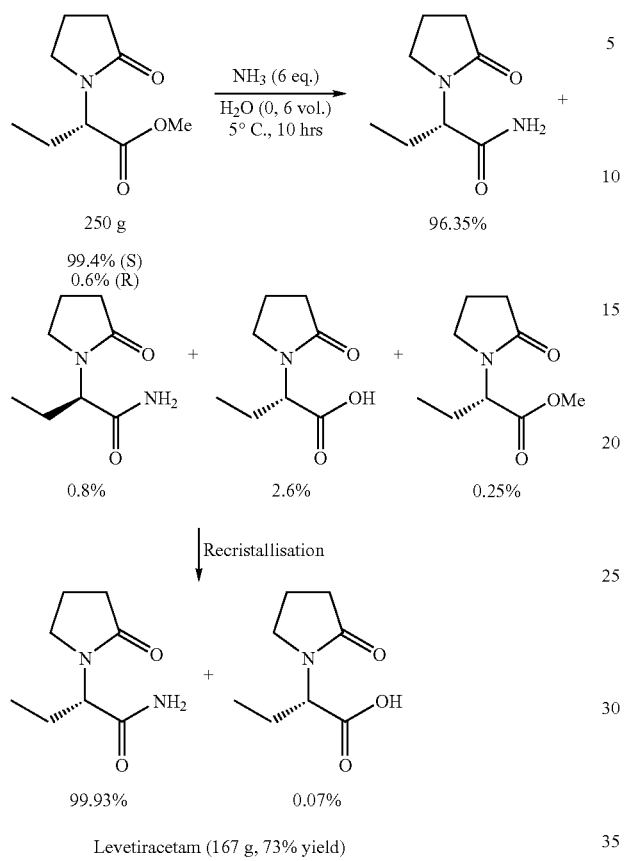

In summary, it has been shown that Levetiracetam may be obtained via ammonolysis of (S)-PBE in concentrated NH₃ (50% in water) and at 5° C. Scaling-up of this reaction has been successfully demonstrated in 0.6 volumes of water in the presence of 6 equivalents of NH₃. The extent of racemisation varies between 0.4 and 2.0%, that of hydrolysis between 3.5 and 6.6%, with a reaction time of approximately 96 hours.

Alternatively, Levetiracetam may equally be obtained via ammonolysis of (S)-PBM in 0.6 volumes of water containing 6 equivalents of NH₃ and at 5° C. The reaction time is much shorter and can be realised in 8 to 10 hours. The extent of racemisation varies between 0.0 and 0.2% and that of hydrolysis ranges from 1.8 to 3.6%.

Example 8

8.1 Preparation of methyl (2S)-2-[2-oxo-(4S)-4-propyl-1-pyrrolidinyl]butanoate

A reaction flask was charged with 2 g of methyl (Z)-2-[2-oxo-(4S)-4-propyl-1-pyrrolidinyl]-2-butenoate, 20 ml of anhydrous and degassed methanol and 27 mg of (S,S)-Me-DUPHOS/Rh(BF₄). The reaction flask was purged with hydrogen and the hydrogen pressure was adjusted to 10 atm. This reaction mixture was stirred during about 20 hours at room temperature and then concentrated. 1.96 g of methyl (2S)-2-[2-oxo-(4S)-4-propyl-1-pyrrolidinyl]butanoate was obtained.

8.2 Ammonolysis

Ammonia gas was condensed in 2 ml water at 0-5° C. and the temperature of the system was maintained at 0-5° C. 0.68 g of methyl (2S)-2-[2-oxo-(4S)-4-propyl-1-pyrrolidinyl]butanoate obtained such as described above was then added dropwise, maintaining the reaction mixture at 0-5° C. The system was then stirred for 6 hrs, with TLC indicating completion of reaction. After standing overnight at ambient temperature the reaction mixture was concentrated at 40° C. under vacuum and further dried by azyeotropic distillation with toluene to give 150 mg of crude (2S)-2-[2-oxo-(4S)-4-propyl-1-pyrrolidinyl]butanamide.

The invention claimed is:
1. A process for the manufacture of an S isomer of a compound of formula (8)

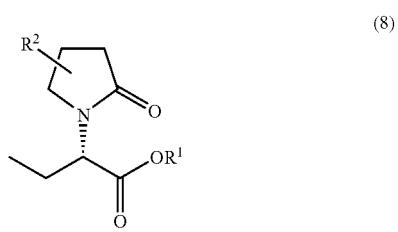

wherein
$R^1$ is methyl or ethyl; and
$R^2$ is $C_2$-$C_4$ alkyl, $C_2$-$C_4$ alkenyl or $C_2$-$C_4$ alkynyl, optionally substituted by one or more halogen; said process comprising the following steps:
(a) reacting a compound of formula (9)

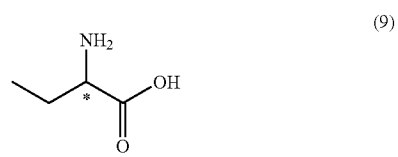

with an alcohol of formula $R^1OH$, wherein $R^1$ is as defined for the compound of formula (8), and thionyl chloride, to obtain a compound of formula (10),

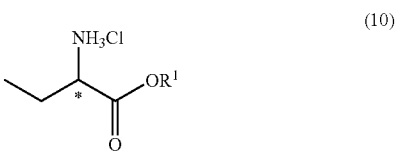

(b) reacting the compound of formula (10) with a $R^2$-substituted-ethyl-4-bromobutyrate, wherein $R^2$ is as defined for the compound of formula (8), to obtain a compound of formula (11),

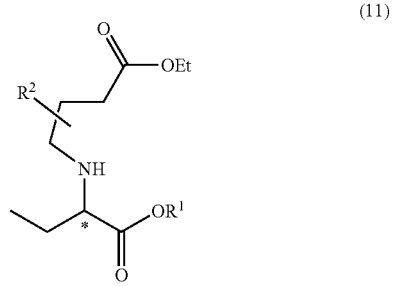

(c) cyclisation of the compound of formula (11) with a catalyst, and
(d) isolating the S isomer of the compound of formula (8).

2. The process according claim 1, wherein step (b) is performed in the presence of a base and an alcohol.

3. The process according to claim 1, wherein the catalyst used in step (c) is pyridinol.

4. A process for the manufacture of an S isomer of a compound of formula (8)

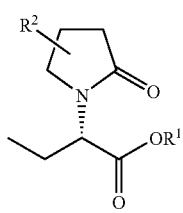
(8)

wherein
R¹ is methyl or ethyl; and
R² is $C_2$-$C_4$ alkyl, $C_2$-$C_4$ alkenyl or $C_2$-$C_4$ alkynyl, optionally substituted by one or more halogen, said process comprising a step of cyclisation of a compound of the formula (11)

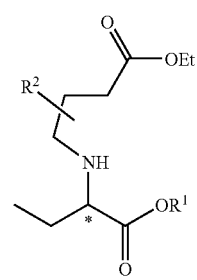
(11)

wherein R¹ and R² are as defined for the compound of formula (8).

5. A process for the manufacture of an S isomer of a compound of formula (8)

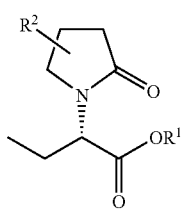
(8)

wherein
R¹ is methyl or ethyl; and
R² is $C_2$-$C_4$ alkyl, $C_2$-$C_4$ alkenyl or $C_2$-$C_4$ alkynyl, optionally substituted by one or more halogen, said process comprising the following steps:

(a) reacting an α-ketocarboxylic acid derivative of formula (12),

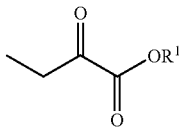
(12)

wherein R¹ is as defined for the compound of formula (8), with a pyrrolidinone of formula (13),

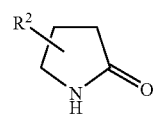
(13)

wherein R² is as defined for the compound of formula (8), to obtain a compound of formula (14),

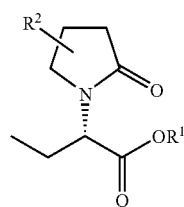
(14)

(b) reacting the compound of formula (14) with hydrogen in the presence of an asymmetric hydrogenation catalyst, and
(c) isolating the S isomer of the compound of formula (8).

6. A process for the manufacture of an S isomer of a compound of formula (8)

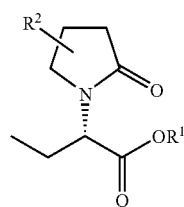
(8)

wherein
R¹ is methyl or ethyl; and
R² is $C_2$-$C_4$ alkyl, $C_2$-$C_4$ alkenyl or $C_2$-$C_4$ alkynyl, optionally substituted by one or more halogen, said process comprising the following steps:
(a) reacting a compound of formula (15),

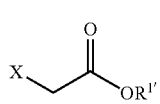
(15)

wherein $R^1$ is $C_1$-$C_6$ alkyl and X is Cl, Br, I, alkylsuiphonate or sulfate, with a pyrrolidone of formula (13),

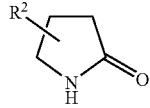
(13)

wherein $R^2$ is as defined for the compound of formula (8), to obtain a compound of formula (16),

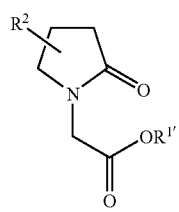
(16)

(b) reacting the compound of formula (16) with ethyl-X, wherein X is Cl, Br, I, alkylsulphonate or sulfate, in the presence of an asymmetric alkylation catalyst or additive, (c) optionally, when $R^{1\prime}$ is different from $R^1$, reacting the compound obtained in step (b) with an alcohol of formula $R^1$ OH, and (d) isolating the S isomer of the compound of formula (8).

7. A process for the manufacture of an S isomer of a compound of formula (8),

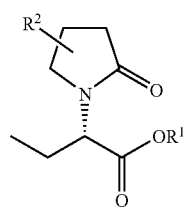
(8)

wherein $R^1$ is methyl or ethyl; and $R^2$ is $C_2$-$C_4$ alkyl, $C_2$-$C_4$ alkenyl or $C_2$-$C_4$ alkynyl, optionally substituted by one or more halogen, said process comprising the following steps:

(a) reacting a compound of general formula (20),

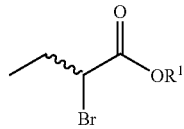
(20)

wherein $R^1$ is as defined for the compound of formula (8), with a pyrrolidone of general formula (13),

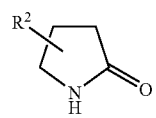
(13)

wherein $R^2$ is defined as for the compound of formula (8), to obtain a compound of formula (21),

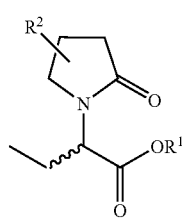
(21)

wherein $R^1$ and $R^2$ are defined as for the compound of formula (8), (b) separating the compound of formula (21), and (c) isolating the S isomer of the compound of formula (8).

* * * * *